United States Patent
Polymeropoulos et al.

(10) Patent No.: US 11,737,993 B2
(45) Date of Patent: Aug. 29, 2023

(54) MULTIPLE MYELOMA TREATMENT

(71) Applicant: Vanda Pharmaceuticals Inc., Washington, DC (US)

(72) Inventors: Mihael H. Polymeropoulos, Potomac, MD (US); Louis William Licamele, Potomac, MD (US); Christian Lavedan, Potomac, MD (US)

(73) Assignee: VANDA PHARMACEUTICALS INC., Washington, DC (US)

( * ) Notice: Subject to any disclaimer, the term of this patent is extended or adjusted under 35 U.S.C. 154(b) by 0 days.

(21) Appl. No.: 16/550,936

(22) Filed: Aug. 26, 2019

(65) Prior Publication Data

US 2020/0009087 A1  Jan. 9, 2020

Related U.S. Application Data

(63) Continuation of application No. 15/979,287, filed on May 14, 2018, now abandoned, which is a continuation of application No. 14/912,078, filed as application No. PCT/US2014/052216 on Aug. 22, 2014, now abandoned.

(60) Provisional application No. 61/870,747, filed on Aug. 27, 2013, provisional application No. 61/869,039, filed on Aug. 22, 2013.

(51) Int. Cl.
| | |
|---|---|
| *A61K 31/165* | (2006.01) |
| *A61P 35/00* | (2006.01) |
| *A61K 9/00* | (2006.01) |

(52) U.S. Cl.
CPC .......... *A61K 31/165* (2013.01); *A61K 9/0019* (2013.01); *A61K 9/0053* (2013.01); *A61P 35/00* (2018.01)

(58) Field of Classification Search
CPC .................................................. A61K 31/165
See application file for complete search history.

(56) References Cited

U.S. PATENT DOCUMENTS

| | | | |
|---|---|---|---|
| 4,218,478 A | 8/1980 | Omura et al. | |
| 2005/0260664 A1* | 11/2005 | Shaughnessy | C12Q 1/6886 435/6.14 |
| 2009/0123925 A1* | 5/2009 | Collie-Duguid | C12Q 1/6886 435/6.12 |

FOREIGN PATENT DOCUMENTS

| | | | |
|---|---|---|---|
| EP | 0196415 A2 | 10/1986 | |
| WO | 02060430 A1 | 8/2002 | |
| WO | 2007067516 A2 | 6/2007 | |
| WO | 2007139939 A2 | 12/2007 | |
| WO | WO-2007139939 A2 * | 12/2007 | ........... A61K 31/165 |
| WO | WO-2010064016 A2 * | 6/2010 | ........... C12Q 1/6886 |

OTHER PUBLICATIONS

Heller (Cancer Research vol. 68 pp. 44-54 published 2008) (Year: 2008).*
Ahn (Oncology Reports vol. 27 p. 455-460 published 2012) (Year: 2012).*
Nair (Cancer Letters vol. 166 pp. 55-64 published 2001). (Year: 2001).*
Ahn (Oncology Reports vol. 27 pp. 455-460. Published 2012). (Year: 2012).*
Reagan-Shaw (FASEBJ vol. 22 pp. 659-661. Published 2007). (Year: 2007).*
Nara (PLOS One vol. 8 p. 1-13, published online Mar. 4, 2013). (Year: 2013).*
Zhang (Cancer Biology and Therapy vol. 7 pp. 1388-1397 published 2008). (Year: 2008).*
Reagan-Shaw et al. (FASEBJ vol. 22 pp. 659-661. Published 2007). (Year: 2007).*
Heller et al., "Genome-Wide Transcriptional Response to 5-Aza-2'-Deoxycytidine and Trichostatin A in Multiple Myeloma Cells," Cancer Research. 68(1):44-54 (2008).
Moreaux et al., "Gene expression-based prediction of myeloma cell sensitivity to histone deacetylase inhibitors," British Journal of Cancer. 109(3):676-85 (2013).
Nara et al., "Bortezomib Reduces the tumorigenicity of Multiple Myeloma via Downregulation of Upregulated Targets in Clonogenic Side Population Cells," PLOS One. 8(3):e56954 (2013).
Shaughnessy, "Amplification and overexpression of CKS1B at chromosome band 1q21 is associated with reduced levels of p27<KiP1> and an aggressive clinical course in multiple myeloma," Hematology. 10(1):117-26 (2005).
International Search Report and Written Opinion for PCT/US2014/052216, dated Nov. 3, 2014, 10 pages.
Office Action and English Translation thereof for Eurasian Patent Application No. 201690446/28 dated Nov. 28, 2016, 4 pages.
Office Action for U.S. Appl. No. 14/912,078 dated Nov. 14, 2017, 23 pages.
Reagan-Shaw et al., "Does translation from animal to human studies revisited," The FASEB Journal, Life Sciences Forum, vol. 22, pp. 659-661, Year 2007.
Gorgun et al., A novel Aurora-A kinase inhivitor MLN8237 induces cytotoxicity and cell-cycle arrest in multiple myeloma,: Blood, vol. 115, pp. 5202-5213, Year 2010.
Chang et al., "Multiple myeloma patients with CKS1B gene amplification have a shorter progression-free survival post-autologous stem cell transplantation," British Journal of Haematology, vol. 135, 486-491, 2006.
Legartova et al., "Expression of RAN, ZHX-2, and CHC1L genes in multiple myeloma patients and in myeloma cell lines treated with HDAC and Dnmts inhibitors," Neoplasma vol. 57, No. 5 482-487.

(Continued)

*Primary Examiner* — Theodore R. Howell
*Assistant Examiner* — George W Kosturko
(74) *Attorney, Agent, or Firm* — Hoffman Warnick LLC

(57) ABSTRACT

The invention relates generally to the treatment of multiple myeloma. One embodiment of the invention provides a method of treating multiple myeloma (MM) in an individual, the method comprising: administering to the individual an effective amount of trichostatin A (TSA).

13 Claims, No Drawings

(56) References Cited

OTHER PUBLICATIONS

Liu et al., "Trichostatin A Affects Breast Cancer Cell Viability by Modulating Fhit and Survivin Expression," Biomedical Engineering and Biotechnology (ICBEB), 2012 International Conference on, IEEE. pp. 1133-1135 (2012).
Vigushin, "Trichostatin A is a histone deacetylase inhibitor with potent antitumor activity against breast cancer in vivo," Clinical Cancer Research. p. 971 (2001).
Park et al., "Inhibitors of histone deacetylases induce tumor-selective cytotoxicity through modulating Aurora-A kinase," Journal of Molecular Medicine. 86(1):117-28 (2007).
Shaughnessy et al., "A validated gene expression model of high-risk multiple myeloma is defined by deregulated expression of genes mapping to chromosome 1," The American Society of Hematology, Blood, Mar. 15, 2007, vol. 109, No. 6.
Ling et al., "Mechanisms of Proteasome Inhibitor PS-341-induced G2-M-Phase Arrest and Apoptosis in Human Non-Small Cell Lung Cancer Cell Lines," Clinical Cancer Research 9: 1145-1154 (2003).
Park et al., "Inhibitors of histone deacetylases induce tumor-selective cytotoxicity through modulating Aurora-A kinase," Journal of Molecular Medicine 86:117-128 (2008).

\* cited by examiner

MULTIPLE MYELOMA TREATMENT

CROSS-REFERENCE TO RELATED APPLICATIONS

This application is a continuation application of U.S. patent application Ser. No. 15/979,827, filed 14 May 2018, which is a continuation of then U.S. patent application Ser. No. 14/912,078, filed 12 Feb. 2016, which is the US National Phase of PCT/US14/52216, filed 22 Aug. 2014, which claims priority to then US Provisional Patent Application Ser. Nos. 61/869,039, filed 22 Aug. 2013 and 61/870,747, filed 27 Aug. 2013, each of which is incorporated herein.

BACKGROUND

Multiple myeloma (MM), sometimes referred to as plasma cell myeloma, is a multifocal plasma cell cancer of the osseous system, generally affecting elderly individuals. Most individuals are symptomatic when diagnosed, with diagnosis typically made by one or more of serum protein electrophoresis, serum free kappa/lambda light chain assay, urine protein electrophoresis (99% of patients with MM exhibit increased levels of one of the immunoglobulin (Ig) classes in the blood and/or light chains in the urine), bone marrow examination, or X-ray analysis. Although MM generally responds to chemotherapy, recurrence is common, since such treatment does not target cancer stem cells.

Nara et al. have recently identified a number of candidate genes for targeting MM tumor-initiating subpopulation (SP) cells, i.e., cancer stem cells. These include a number of genes coding for proteins associated with cell cycle and mitosis, all of which were found to be upregulated in MM cells. These include cyclin B1 (CCNB1), cell division cycle 2 (CDC2), baculoviral IAP repeat-containing 5 (BIRC5), abnormal spindle homolog, microcephaly-associated (ASPM), topoisomerase (DNA) II alpha 170 kDa (TOP2A), aurora kinase B (AURKB), kinesin family member 11 (KIF11), and kinesin family member 2c (KIF2C).

Similarly, Shaughnessy et al. report a 70-gene high-risk profile for multiple myeloma. Two of the genes upregulated in this high-risk profile are CDC28 protein kinase regulatory subunit 1B (CKS1B) and WEE1 homolog (*S. pombe*) (WEE1).

SUMMARY

One embodiment of the invention provides a method of treating multiple myeloma (MM) in an individual, the method comprising: administering to the individual an effective amount of trichostatin A (TSA).

In another embodiment, the invention provides a method of treating multiple myeloma (MM) in an individual, the method comprising: determining, from a biological sample obtained from the individual's body, a level of expression of at least one gene selected from a group consisting of: CCNB1, AURKB, CDC2, BIRC5, KIF11, KIF2C, TOP2A, ASPM, CKS1B, and WEE1; and in the case that the level of expression of the at least one gene is indicative of overexpression, administering to the individual an effective amount of trichostatin A (TSA).

In yet another embodiment, the invention provides a method of treating multiple myeloma (MM) in an individual, the method comprising: diagnosing or having diagnosed the individual with MM; and administering to the individual an effective amount of trichostatin A (TSA).

In still yet another embodiment, the invention provides a pharmaceutical composition comprising: trichostatin A (TSA) as a sole or primary inhibitor of CCNB1, AURKB, CDC2, BIRC5, KIF11, KIF2C, TOP2A, ASPM, CKS1B, or WEE1; and a pharmaceutically-acceptable excipient or carrier.

In still other embodiments of the invention, treatment with TSA is combined with one or more other multiple myeloma treatments. Such other treatments may include, for example, small molecule inhibition.

DETAILED DESCRIPTION

Trichostatin A (TSA or 7-[4-(dimethylamino)phenyl]-N-hydroxy-4,6-dimethyl-7-oxohepta-2,4-dienamide), is an antifungal antibiotic. The structure of TSA is shown in Formula I below.

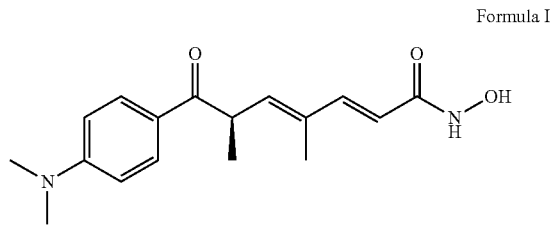 [SMILES: CC(/C=C/C(=O)NO)=C\[C@@H](C)C(=O)c1ccc(N(C)C)cc1]

Formula I

Applicants have surprisingly found that TSA, although previously known as a class I and II histone deacetylase (HDAC) inhibitor, is also capable of inhibiting expression of CCNB1, AURKB, CDC2, BIRC5, KIF11, KIF2C, TOP2A, ASPM, CKS1B, and WEE1. Accordingly, TSA may be used as a primary or sole inhibitor of one or more such genes in the treatment of MM.

A human retinal pigment epithelial cell line was treated with trichostatin or vehicle for 24 hours and gene expression for 22,238 probe sets covering 12,490 genes was generated using an Affymetrix instrument. The effect of trichostatin A on expression of CCNB1, AURKB, CDC2, BIRC5, KIF11, KIF2C, TOP2A, ASPM, CKS1B, and WEE1 is shown below in Table 1, and indicates significant downregulation of the expression of each gene.

TABLE 1

| Instance ID | Probe | Rank | Fold Expression Δ | Gene |
|---|---|---|---|---|
| 10005542 | 219918_s_at | 22283 | −69.97232079 | ASPM |
| 10005533 | 219918_s_at | 22282 | −54.61735261 | ASPM |
| 10005532 | 219918_s_at | 22261 | −23.24977266 | ASPM |
| 10005542 | 209464_at | 22190 | −11.52858083 | AURKB |
| 10005533 | 209464_at | 22185 | −11.04347695 | AURKB |
| 10005542 | 202095_s_at | 22270 | −24.2000252 | BIRC5 |
| 10005533 | 202095_s_at | 22256 | −23.02258123 | BIRC5 |
| 10005533 | 202094_at | 22251 | −20.74385736 | BIRC5 |
| 10005532 | 202095_s_at | 22252 | −19.95557418 | BIRC5 |
| 10005542 | 202094_at | 22227 | −14.71770993 | BIRC5 |
| 10005532 | 202094_at | 22219 | −14.42912247 | BIRC5 |
| 10005533 | 214710_s_at | 22267 | −26.45555632 | CCNB1 |
| 10005533 | 214710_s_at | 22267 | −26.32053821 | CCNB1 |
| 10005542 | 214710_s_at | 22251 | −20.15506664 | CCNB1 |
| 10005532 | 203213_at | 22270 | −27.14720991 | CDC2 |
| 10005533 | 203213_at | 22260 | −23.81235655 | CDC2 |
| 10005542 | 203213_at | 22253 | −20.26528442 | CDC2 |
| 10005533 | 210559_s_at | 22199 | −12.07146825 | CDC2 |
| 10005532 | 210559_s_at | 22192 | −11.92448867 | CDC2 |
| 10005533 | 203214_x_at | 22194 | −11.8262682 | CDC2 |
| 10005542 | 204444_at | 22213 | −13.12379506 | KIF11 |
| 10005532 | 204444_at | 22187 | −11.4579544 | KIF11 |

TABLE 1-continued

| Instance ID | Probe | Rank | Fold Expression Δ | Gene |
|---|---|---|---|---|
| 10005533 | 204444_at | 22184 | −10.96422696 | KIF11 |
| 10005533 | 209408_at | 22250 | −19.89427497 | KIF2C |
| 10005532 | 209408_at | 22248 | −19.35105571 | KIF2C |
| 10005542 | 209408_at | 22224 | −14.47328923 | KIF2C |
| 10005532 | 201292_at | 22274 | −31.9462153 | TOP2A |
| 10005533 | 201291_s_at | 22270 | −28.21627346 | TOP2A |
| 10005532 | 201897_s_at | 22279 | −39.94584911 | CKS1B |
| 10005533 | 201897_s_at | 22279 | −52.93016044 | CKS1B |
| 10005542 | 201897_s_at | 22268 | −23.90194858 | CKS1B |
| 10005532 | 212533_at | 22237 | −17.0758281 | WEE1 |
| 10005533 | 212533_at | 22248 | −19.46663938 | WEE1 |
| 10005542 | 212533_at | 22265 | −23.63054187 | WEE1 |

These results support the use of TSA in the treatment of MM. For example, an individual may be treated for MM by administering to the individual an effective amount of TSA, wherein the effective amount is an amount sufficient to inhibit expression of one or more of CCNB1, AURKB, CDC2, BIRC5, KIF11, KIF2C, TOP2A, ASPM, CKS1B, and WEE1 in the individual. Such an amount may also be sufficient to inhibit HDAC activity in the individual. In some embodiments of the invention, the effective amount is between about 0.01 mg/kg/day and about 100 mg/kg/day, e.g., between about 0.1 mg/kg/day and about 10 mg/kg/day or between about 0.5 mg/kg/day and about 5 mg/kg/day.

In some embodiments, treating the individual may further comprise determining, from a biological sample obtained from the individual's body, a level of expression of one or more of CCNB1, AURKB, CDC2, BIRC5, KIF11, KIF2C, TOP2A, ASPM, CKS1B, or WEE1. Such determining may include any known or later-developed method or technique, including, for example, quantitative antigen-antibody interactions, the use of labeled nucleotide probes, etc.

In other embodiments of the invention, treating the individual may include diagnosing or having diagnosed the individual with MM prior to administering TSA to the individual. Such diagnosing may include one or more technique or method for making such a diagnosis, including, for example, serum protein electrophoresis, serum free kappa/lambda light chain assay, urine protein electrophoresis, bone marrow examination, or X-ray analysis.

TSA may be administered to the individual to be treated in the form of a pharmaceutical composition. Pharmaceutical compositions to be used according to various embodiments of the invention comprise a therapeutically effective amount of TSA or an active metabolite of TSA, or a pharmaceutically acceptable salt or other form (e.g., a solvate) thereof, together with one or more pharmaceutically acceptable excipients or carriers. The phrase "pharmaceutical composition" refers to a composition suitable for administration in medical use. It should be appreciated that the determinations of proper dosage forms, dosage amounts, and routes of administration for a particular patient are within the level of ordinary skill in the pharmaceutical and medical arts.

Administration may be oral but other routes of administration may also be employed, e.g., parenteral, nasal, buccal, transdermal, sublingual, intramuscular, intravenous, rectal, vaginal, etc. Solid dosage forms for oral administration include capsules, tablets, pills, powders, and granules. In such solid dosage forms, the compound is admixed with at least one inert pharmaceutically-acceptable excipient such as (a) fillers or extenders, as for example, starches, lactose, sucrose, glucose, mannitol, and silicic acid, (b) binders, as for example, carboxymethylcellulose, alginates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid dosage forms such as tablets, drages, capsules, pills, and granules also can be prepared with coatings and shells, such as enteric coatings and others well known in the art. The solid dosage form also may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients. Such solid dosage forms may generally contain from 1% to 95% (w/w) of the active compound. In certain embodiments, the active compound ranges from 5% to 70% (w/w).

Solid compositions for oral administration can be formulated in a unit dosage form, each dosage containing from about 0.1 mg to about 5000 mg of active ingredient. The term "unit dosage form" refers to physically discrete units suitable as unitary dosages for human subjects and other mammals, each unit containing a predetermined quantity of active ingredient calculated to produce the desired effect over the course of a treatment period, in association with the required pharmaceutical carrier. TSA can be formulated, e.g., in a unit dosage form that is a capsule having 0.1-5000 mg of active in addition to excipients.

Liquid dosage forms for oral administration include pharmaceutically-acceptable emulsions, solutions, suspensions, syrups, and elixirs. In addition to the compound or composition, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances. Besides such inert diluents, the composition can also include adjuvants, such as wetting agents, emulsifying and suspending agents, sweetening, flavoring, and perfuming agents.

In some embodiments of the invention, TSA is provided in a liquid form and administered to an individual intravenously. According to some embodiments of the invention, TSA is provided in a sustained or controlled release formulation.

While this invention has been described in conjunction with the specific embodiments outlined above, it is evident that many alternatives, modifications and variations will be apparent to those skilled in the art or are otherwise intended to be embraced. Accordingly, the embodiments of the invention as set forth above are intended to be illustrative, not limiting. Various changes may be made without departing from the spirit and scope of the invention as defined in the following claims. All patents, patent application, scientific articles and other published documents cited herein are hereby incorporated in their entirety for the substance of their disclosures.

What is claimed is:

1. A method of treating a patient suffering from multiple myeloma (MM), the method comprising:
   determining or having determined, from a biological sample obtained from the patient's body, that a level of expression of one or more gene selected from a group consisting of: AURKB, BIRC5, KIF11, KIF2C, TOP2A, ASPM, CKS1B, and WEE1 is indicative of overexpression; and
   administering to the patient an effective amount of trichostatin A (TSA),
   wherein the effective amount is between about 0.01 mg/kg/day and about 100 mg/kg/day and effective to decrease expression of the one or more gene.

2. The method of claim 1, wherein the effective amount is an amount sufficient to decrease expression of each of AURKB, BIRC5, KIF11, KIF2C, TOP2A, ASPM, CKS1B, and WEE1.

3. The method of claim 1, wherein the effective amount is between about 0.1 mg/kg/day and about 10 mg/kg/day.

4. The method of claim 3, wherein the effective amount is between about 0.5 mg/kg/day and about 5 mg/kg/day.

5. In a method of treating multiple myeloma (MM) with trichostatin A (TSA), the improvement comprising:
   selecting for treatment with between about 0.01 mg/kg and about 100 mg/kg per day of TSA a patient determined to overexpress at least one gene selected from a group consisting of: AURKB, BIRC5, KIF11, KIF2C, TOP2A, ASPM, CKS1B, and WEE1.

6. The improvement of claim 5, wherein the amount of TSA is effective to decrease expression of the at least one gene.

7. The improvement of claim 6, wherein the amount is effective to decrease expression of AURKB.

8. The improvement of claim 6, wherein the amount is effective to decrease expression of either or both of CKS1B and WEE1.

9. The improvement of claim 6, wherein the amount is effective to decrease expression of each of AURKB, BIRC5, KIF11, KIF2C, TOP2A, ASPM, CKS1B, and WEE1.

10. The improvement of claim 5, wherein the amount is between 0.1 mg/kg/day and 10 mg/kg/day.

11. The improvement of claim 10, wherein the amount is between 0.5 mg/kg/day and 5 mg/kg/day.

12. The improvement of claim 5, wherein the TSA is administered orally.

13. The improvement of claim 5, wherein the TSA is administered intravenously.

* * * * *